US011696699B2

(12) United States Patent
Kremeier et al.

(10) Patent No.: US 11,696,699 B2
(45) Date of Patent: Jul. 11, 2023

(54) SYSTEM, VENTILATOR AND METHOD FOR REAL-TIME DETERMINATION OF A LOCAL STRAIN OF A LUNG DURING ARTIFICIAL VENTILATION

(71) Applicant: Loewenstein Medical Technology S.A., Luxembourg (LU)

(72) Inventors: Peter Kremeier, Karlsruhe (DE); Gerado Tusman, Mar del Plata (AR); Sven Pulletz, Osnabrueck (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 540 days.

(21) Appl. No.: 16/847,752

(22) Filed: Apr. 14, 2020

(65) Prior Publication Data
US 2020/0324067 A1    Oct. 15, 2020

(30) Foreign Application Priority Data

Apr. 15, 2019 (DE) .......................... 102019109932.3

(51) Int. Cl.
*A61B 5/0536* (2021.01)
*A61M 16/00* (2006.01)
(Continued)

(52) U.S. Cl.
CPC .......... *A61B 5/0536* (2013.01); *A61B 5/004* (2013.01); *A61B 5/0036* (2018.08);
(Continued)

(58) Field of Classification Search
CPC ..... A61B 5/0036; A61B 5/004; A61B 5/0536; A61B 5/0803; A61B 5/0809; A61B 5/085; A61B 5/743; A61M 16/00; A61M 16/0057; A61M 16/0066; A61M 16/024; A61M 2230/46; A61M 2230/65; G06T 2207/30061
See application file for complete search history.

(56) References Cited

U.S. PATENT DOCUMENTS

2006/0260611 A1   11/2006   Garber et al.
2015/0287186 A1*  10/2015   Holzhacker ............ A61B 5/743
                                                          382/131
(Continued)

FOREIGN PATENT DOCUMENTS

DE    102005022896 B3    5/2006
DE    102013203177 A1    8/2014
DE    102015006902 B3    6/2016

*Primary Examiner* — Joseph D. Boecker
(74) *Attorney, Agent, or Firm* — Abel Schillinger, LLP

(57) ABSTRACT

The present invention relates to a system for real-time determination of a local strain of a lung during artificial ventilation. The system comprises a device for electrical impedance tomography (EIT), which device is configured to capture an electrical impedance distribution along at least one two-dimensional section through a human thorax, and further comprises a device for assigning the captured electrical impedance distribution, which device is configured to divide the captured electrical impedance distribution at different times during the artificial ventilation into a multiplicity of EIT pixels and to assign a specific value of the electrical impedance at a specific time to a specific EIT pixel.

13 Claims, 3 Drawing Sheets

(51) Int. Cl.
*A61B 5/08* (2006.01)
*A61B 5/085* (2006.01)
*A61M 16/06* (2006.01)
*A61B 5/00* (2006.01)

(52) U.S. Cl.
CPC ............ *A61B 5/0803* (2013.01); *A61B 5/085* (2013.01); *A61B 5/0809* (2013.01); *A61B 5/743* (2013.01); *A61M 16/0057* (2013.01); *A61M 16/024* (2017.08); *A61B 5/0816* (2013.01); *A61M 16/0066* (2013.01); *A61M 16/0683* (2013.01); *A61M 2016/0027* (2013.01); *A61M 2016/0033* (2013.01); *A61M 2205/52* (2013.01); *A61M 2230/46* (2013.01); *A61M 2230/65* (2013.01); *G06T 2207/30061* (2013.01)

(56) References Cited

U.S. PATENT DOCUMENTS

| | | | |
|---|---|---|---|
| 2016/0008561 A1* | 1/2016 | Novotni | A61B 5/0809 |
| | | | 128/204.23 |
| 2016/0354007 A1 | 12/2016 | Garber | |
| 2019/0038173 A1* | 2/2019 | Gärber | A61B 5/0871 |
| 2021/0244901 A1* | 8/2021 | Kremeier | A61B 5/0809 |

\* cited by examiner

SYSTEM, VENTILATOR AND METHOD FOR REAL-TIME DETERMINATION OF A LOCAL STRAIN OF A LUNG DURING ARTIFICIAL VENTILATION

CROSS-REFERENCE TO RELATED APPLICATIONS

The present application claims priority under 35 U.S.C. § 119 of German Patent Application No. 102019109932.3, filed Apr. 15, 2019, the entire disclosure of which is expressly incorporated by reference herein.

BACKGROUND OF THE INVENTION

1. Field of the Invention

The present invention relates to a system for real-time determination of a local strain of a lung during artificial ventilation. Further, the invention relates to a system for automatically setting a value specified by a ventilator, in particular a pressure, preferably a positive end-expiratory pressure (PEEP), comprising an aforementioned system for real-time determination of a local strain of a lung during artificial ventilation, and, furthermore, to a ventilator comprising an aforementioned system for automatically setting a value specified by a ventilator. Furthermore, the invention relates to a method for determining a local strain of a lung during artificial ventilation, and to a method for automatically setting a value specified by a ventilator, and to a corresponding ventilator.

2. Discussion of Background Information

In the case of machine-driven ventilation of patients by means of a ventilator, the patient is supplied respiratory gas at positive pressure. As a result of this, the airway pressure or alveolar pressure is greater than the pressure in the pleural cavity surrounding the air vesicles or alveoli during ventilation, at least during the inspiration phase. When the application of pressure on the airways by the ventilation device is retracted again during the expiration phase, this has the consequence that the lung tissue expands and the airway pressure or alveolar pressure drops. Under certain circumstances, this type of positive pressure ventilation can lead to such disadvantageous pressure conditions in the airways or in the alveoli setting in at the end of the expiration phase that this leads to a collapse of some of the alveoli. Then, the collapsed part of the lung volume must first of all be unfolded again during the subsequent respiratory cycle. This impairs the functional residual capacity of the lung, and so the oxygen saturation reduces and even the lung tissue can be damaged in the process.

In order to prevent a collapse of alveoli at the end of the expiration phase, a so-called positive end-expiratory pressure—abbreviated PEEP below—is often set during machine-driven positive pressure ventilation.

During artificial ventilation with PEEP, the ventilation device applies at least a predetermined positive pressure, the PEEP, on the airways on a permanent basis—i.e., both during the inspiration phase and during the expiration phase. Thus, the PEEP is still applied after the end of the expiration phase.

The goal is to set the PEEP in such a way, where possible, that the alveolar pressure during the expiration phase does not drop below the pressure in the pleural cavity or at least only drops so far below said pressure that the alveolar tissue does not collapse under the action of the pressure in the pleural cavity. However, a value of the PEEP that is too high can have negative consequences, particularly during the inspiration phase. This is because the lung tissue can be overextended in the case of very high airway pressures during the inspiration phase. Locally, there is too great a strain of the lung.

It is therefore desirable to observe the strain of the lung as accurately as possible in order to be able to draw conclusions about a PEEP that may have been set too high or too low—or about other parameters characterizing the artificial ventilation.

In the prior art, it is conventional to specify the load on the lung as a so-called strain, by virtue of the tidal volume being related to the functional residual capacity of the lung. Consequently, the strain of the lung (STR) can be determined by way of the following equation:

$$STR = Tidal\ volume/FRC$$

STR: strain
FRC: functional residual capacity

However, a problem when determining the strain of the lung in such a way is, firstly, that the functional residual capacity can only be determined with difficulties, especially during artificial ventilation of a patient. Secondly, such an aforementioned determination of the strain of the lung only supplies a global value for the strain of the lung. It is not possible to have local resolution in respect of which regions of the lung are under more strain and which are under less strain. It is not possible to make deductions about locally over-expanded lung regions or locally collapsed sections of the lung.

Electrical impedance tomography—abbreviated EIT below—can offer a remedy at this juncture. EIT is an imaging method that can be used to draw conclusions about the state of the lung of a patient in non-invasive fashion. What is exploited to this end is the fact that the change of an impedance signal obtained by EIT, which is influenced by respiratory movements of the patient, is greater in regions where the lung has not yet collapsed than in regions with collapsed alveoli.

EIT makes a method available that allows information about the state of the lung, in particular about the opening and closing of alveoli or an overexpansion of alveoli, to be obtained in real time. EIT can be performed directly at the patient's bed and supplies spatially differentiated information in respect of different regions of the lung. For details about EIT, reference may also be made to document DE 10 2013 203 177 A1, the entire disclosure of which is expressly incorporated by reference herein.

It is now desirable to be able to deduce conclusions about the local strain of a lung during artificial ventilation in the simplest possible manner, ideally in order also to derive instructions for the parameters to be set for the artificial ventilation.

In view of the foregoing, it would be advantageous to have available a system for real-time determination of a local strain of a lung during artificial ventilation, which can represent the local strain of the lung in non-invasive, quick and reliable fashion.

It further would be advantageous to have available a system for automatically setting a value specified by a ventilator, which can control the artificial ventilation of the lung in quick and reliable fashion.

It further would be advantageous to have available a ventilator that can perform artificial ventilation of the lung in reliable fashion, with the risk of overexpansion or collapse of regions of the lung being reduced.

It further would be advantageous to have available a method for determination of a local strain of a lung during artificial ventilation, by means of which the local strain of the lung can be determined in non-invasive, quick and reliable fashion.

It further would be advantageous to have available a method for automatically setting a value specified by a ventilator, by means of which the artificial ventilation of the lung can be controlled in reliable fashion.

SUMMARY OF THE INVENTION

The present invention provides, inter alia, a system for real-time determination of a local strain of a lung during artificial ventilation, a system for automatically setting a value specified by a ventilator, a ventilator, a method for determining a local strain of a lung during artificial ventilation, and a method for automatically setting a value specified by a ventilator.

The dependent claims relate to various mutually independent, advantageous developments of the present invention, the features of which, within the scope of what is technically feasible, can be combined freely with one another by a person skilled in the art. In particular, this also applies beyond the boundaries of the various claim categories.

In detail, a system for real-time determination of a local strain of a lung during artificial ventilation is proposed according to a first aspect of the invention. The system comprises a device for electrical impedance tomography (EIT), which is configured to capture an electrical impedance distribution along at least one two-dimensional section through a human thorax. Further, a device for assigning the captured electrical impedance distribution is provided, said device being configured to divide the captured electrical impedance distribution at different times during the artificial ventilation into a multiplicity of EIT pixels and to assign a specific value of the electrical impedance at a specific time to a specific EIT pixel. Furthermore, a device for determining a local strain value is provided. The latter is configured to determine at least one end-inspiratory electrical impedance ($Z_{INSP}$) of the specific EIT pixel and an end-expiratory electrical impedance ($Z_{EXSP}$) of the specific EIT pixel. Further, said device is configured to form a local tidal volume reference value ($\Delta Z$) of the specific EIT pixel as a difference between the end-inspiratory electrical impedance ($Z_{INSP}$) and the end-expiratory electrical impedance ($Z_{EXSP}$). Furthermore, said device is configured to form a preliminary strain value ($STR_{VORL}$) of the specific EIT pixel by dividing the local tidal volume reference value ($\Delta Z$) by the end-expiratory electrical impedance ($Z_{EXSP}$). Finally, the device for determining a local strain value is further configured to form a relative strain value ($STR_{RELATIV}$) of the specific EIT pixel by normalizing the preliminary strain value ($STR_{VORL}$) to a reference strain value ($STR_{REF}$).

What is important to the present invention is that a spatially resolved observation of the lung can be made in respect of possible overexpansion with the aid of the system described. Moreover, this observation can be made in real time, during artificial ventilation. This can be implemented without requiring complicated interventions to the detriment of the patient since EIT is a non-invasive, imaging method.

As a result of the captured impedance values being able to be used as reference values for a volume present in a specific EIT pixel, it is possible to locally determine an analogous value for the tidal volume in the specific EIT pixel, with a resolution of individual regions of the lung.

If this reference impedance value that represents the tidal volume is related to the reference impedance value that represents the remaining volume in the same EIT pixel, it is possible to obtain a value that reproduces the strain in this specific region of the lung. Thus, instead of the global determination of the strain according to the prior art, it is now possible to obtain a local resolution and the local strain can be determined.

This local determination is implemented accordingly for a specific EIT pixel according to the following equation:

$$STR_{VORL} = \Delta Z / Z_{EXSP}$$

$STR_{VORL}$: preliminary strain value
$\Delta Z$: local tidal volume reference value
$Z_{EXSP}$: end-expiratory electrical impedance In order to determine the local tidal volume reference value ($\Delta Z$) of the specific EIT pixel, it is possible, in particular, to subtract the end-expiratory electrical impedance ($Z_{EXSP}$) from the end-inspiratory electrical impedance ($Z_{INSP}$).

By means of the present system, it is possible to determine the end-inspiratory electrical impedance ($Z_{INSP}$) and the end-expiratory electrical impedance ($Z_{EXSP}$). From this, it is possible to determine the difference as a representative for the local tidal volume in the specific lung region. Finally, by relating this reference to the end-expiratory electrical impedance ($Z_{EXSP}$)—representing the remaining volume in the specific region—again, it is possible to obtain a value representing the strain of the lung region.

The end-expiratory electrical impedance ($Z_{EXSP}$) in this case corresponds to the final value of the electrical impedance at the end of expiration in the specific EIT pixel. It can also be abbreviated EELI.

This value, representing the strain of the specific lung region, is referred to as "preliminary strain value" in the present case. Finally, this preliminary strain value can still be normalized by means of the system present. Such a normalization means that a quotient is formed using the preliminary strain value and a reference strain value ($STR_{REF}$). Finally, this obtains a relative strain value that represents the local strain of the lung.

The normalization affords comparability by virtue of the specific preliminary strain value determined in real time being related to a reference strain value, which represents the "open lung" state. Here, "open lung" means that the lung is neither collapsed nor over-expanded. Thus, the specifically determined, preliminary strain value is normalized by virtue of being related to a value representing the lung in an approximately normal state. This obtains a relative strain value that represents the local strain of the lung.

According to a first advantageous embodiment, the reference strain value ($STR_{REF}$) can be a quotient of the local tidal volume reference value ($\Delta Z$) and the end-expiratory electrical impedance ($Z_{EXSP}$) of the specific EIT pixel at a specified positive end-expiratory pressure (PEEP). Accordingly, the device for determining a local strain value for forming the relative strain value ($STR_{RELATIV}$) of the specific EIT pixel can be embodied in such a way that the preliminary strain value ($STR_{VORL}$) can be normalized to a quotient of the local tidal volume reference value ($\Delta Z$) and the end-expiratory electrical impedance ($Z_{EXSP}$) of the specific EIT pixel at a specified positive end-expiratory pressure (PEEP). This specified positive end-expiratory pressure (PEEP) can be a so-called "open lung PEEP" or, abbreviated, "OL-PEEP". This value for the specified positive end-expiratory pressure in the form of an "open lung PEEP" or "OL-PEEP" allows an end-expiratory collapse of the lung to be avoided. Thus, this embodiment is based on the deliberation that, during artificial ventilation with such a specified PEEP, the conditions in the lung are such that the risk of a collapse of lung regions, but also of overexpansion of lung regions, is minimal. The normalization to this so-called "normal state" allows particularly good online observations of the strain of individual lung regions to be obtained in real time. In this way, it is possible to observe the influence of the PEEP, or else of other parameters controlling the artificial ventilation of the patient, on the local strain of the lung and accordingly control said influence by way of controlling said parameters.

Accordingly, the relative strain value ($STR_{RELATIV}$) of a specific EIT pixel can be determined by way of the following equation:

$$STR_{RELATIV} = STR_{VORL} / (\Delta Z_{OL-PEEP} / Z_{EXSP, OL-PEEP}) =$$
$$(\Delta Z / Z_{EXSP}) / (\Delta Z_{OL-PEEP} / Z_{EXSP, OL-PEEP})$$

$STR_{RELATIV}$: relative strain value
$STR_{VORL}$: preliminary strain value
$\Delta Z_{OL-PEEP}$: tidal volume reference value in the case of OL-PEEP
$Z_{EXSP, OL-PEEP}$: end-expiratory electrical impedance in the case of OL-PEEP
$\Delta Z$: local tidal volume reference value
$Z_{EXSP}$: end-expiratory electrical impedance As reference for the normalization described, use can be made of the quotient of a local tidal volume reference value ($\Delta Z$) and the end-expiratory electrical impedance ($Z_{EXSP}$), for example in the case of a positive end-expiratory pressure of 15 cm $H_2O$. Alternatively, a different positive end-expiratory pressure can also serve as a reference value.

Here, different methods can be applied in order to determine the "OL-PEEP" in advance and finally successfully perform the above-described step of normalization:

Thus, the value where the transmural pressure is greater than 0 can be used as "OL-PEEP"

Likewise, the value where the esophagus pressure is greater than 0 can be used as "OL-PEEP"

An "OL-PEEP" can also be ascertained by means of EIT by virtue of a pressure ramp being driven and the pressure at which there is a sudden increase in the impedance in the dependent lung pixels being determined. This indicates the opening pressure of the pixel region.

An "OL-PEEP" can also be ascertained by means of the so-called "best dynamic compliance technique". In this respect, reference is made to the paper by Suarez-Sipmann (Crit Care Med 2007 Vol. 35, No. 1, pp. 214-221).

An "OL-PEEP" can also be determined by means of a Costa-type EIT. In this respect, reference is made to the paper by Costa (Intensive Care Med; DOI 10.1007/s00134-009-1447-y).

By directly measuring the expiratory lung volume, it is likewise possible to ascertain a reference value for the purposes of normalizing to an approximately normal lung volume (which corresponds the functional residual capacity—FRC—in the case of healthy lungs and a PEEP of 0 in magnitude).

According to a further aspect of the teaching, a system for automatically setting a value specified by a ventilator, in particular a pressure, preferably a positive end-expiratory pressure (PEEP) is proposed, comprising an above-described system, wherein provision is made for a closed-loop control device that is configured to adapt the value specified by the ventilator on the basis of the relative strain values ($STR_{RELATIV}$) formed.

According to a further aspect of the teaching, a ventilator is proposed, comprising such a system for automatically setting a value specified by a ventilator.

According to a further aspect of the teaching, a ventilator for carrying out the methods and/or for use in the systems is proposed.

By transferring the above-described system for real-time determination of a local strain of a lung during artificial ventilation to a ventilator, for example, it is possible to improve the artificial ventilation of a patient to the effect that the knowledge obtained about the local strain of individual lung areas can be used to adapt the ventilation parameters. By way of example, the PEEP can be adapted, in particular, should individual lung areas be determined as being exposed to strain that is too high. By way of example, this can be detected by virtue of the relative strain value being high. By adapting the PEEP (in the form of an increase or reduction, for example), or by adapting other ventilation parameters, it is possible to observe the change in the relative strain value ($STR_{RELATIV}$) in real time. By way of example, another ventilation parameter to be set can be the tidal volume. This is because if the tidal volume provided by the ventilator is reduced, this, as a rule, will also be able to reduce the overexpansion or the strain of the lung. Means can also be provided, for example a closed-loop control device, which automatically adapt the PEEP or other values such as the tidal volume or other values so that a desired, e.g., particularly low, relative strain value ($STR_{RELATIV}$) is present at all times.

According to a further aspect of the teaching, a method for determining a local strain of a lung during artificial ventilation is proposed, in particular for implementation in a system according to either of claims 1 and 2. In the process, the following steps are carried out: capturing an electrical impedance distribution along at least one two-dimensional section through a human thorax by means of a device for electrical impedance tomography (EIT); dividing the captured electrical impedance distribution at different times during the artificial ventilation into a multiplicity of EIT pixels; assigning a specific value of the electrical impedance to a specific EIT pixel at a specific time; determining at least one end-inspiratory electrical impedance ($Z_{INSP}$) of the specific EIT pixel and an end-expiratory electrical impedance ($Z_{EXSP}$) of the specific EIT pixel; forming a local tidal volume reference value ($\Delta Z$) of the specific EIT pixel as a difference between the end-inspiratory electrical impedance ($Z_{INSP}$) and the end-expiratory electrical impedance ($Z_{EXSP}$), in particular by subtracting the end-expiratory electrical impedance ($Z_{EXSP}$) from the end-inspiratory electrical impedance ($Z_{INSP}$); forming a preliminary strain value ($STR_{VORL}$) of the specific EIT pixel by dividing the local tidal volume reference value ($\Delta Z$) by the end-expiratory electrical impedance ($Z_{EXSP}$); and forming a relative strain value ($STR_{RELATIV}$) of the specific EIT pixel by normalizing the preliminary strain value ($STR_{VORL}$) to a reference strain value ($STR_{REF}$).

According to a further advantageous embodiment of the method, the reference strain value ($STR_{REF}$) is formed as a quotient of the local tidal volume reference value ($\Delta Z$) and the end-expiratory electrical impedance ($Z_{EXSP}$) of the specific EIT pixel at a specified positive end-expiratory pressure (PEEP).

The specific effects and advantages of these methods have already been described above in respect of the system for real-time determination of a local strain of a lung during artificial ventilation. In this respect, reference is made thereto.

Further preferably, a relevant lung area can initially be identified in the method. This step can further increase the efficiency of the method. Thus, a preceding step allows exactly the region in which lung tissue to be observed is present in the patient to be captured. The EIT can be optimized accordingly since impedance measurements are only of importance in respect of the areas in which lung tissue is really also present.

To this end, it is possible, for example, to initially undertake reference impedance measurements. By way of example, it is thus possible to determine electrical impedance in the case of artificial ventilation under elevated PEEP. This is because the assumption made in the case of an elevated PEEP is that even lung tissue that may have collapsed will refill with air and unfold and consequently also exhibit a deflection during the impedance measurement. Consequently, all regions that accordingly exhibit a significant impedance difference (for instance in the form of the local tidal volume reference value $\Delta Z$), for example an impedance difference lying above a specified threshold, in the case of an impedance measurement under an elevated PEEP can be identified as relevant lung areas.

Particularly preferably, a plurality of measurements could also be undertaken at different PEEP values for the purposes of identifying the relevant lung area and the pixels that exhibit an aforementioned, significant impedance difference in the respective different measurements could be labeled as relevant lung area. This is because, especially in the case of a low PEEP, there can be ventilation of previously overexpanded air vesicles, predominantly in the gravity-independent upper parts of the lung, while the lowermost lung areas continue to collapse, however. By way of example, these lowermost lung areas only exhibit ventilation at a higher PEEP, which is expressed in a relevant significant impedance difference. Accordingly, a multiplicity of different PEEP values should be set when identifying the relevant lung area and the pixels that exhibit tidal ventilation in at least one of the PEEP levels should be identified as lung pixels.

Accordingly, provision can also be made in the above-described systems for a device for identifying a relevant lung area, which is configured to identify a relevant lung area.

Finally, according to a further aspect of the teaching, a method for automatically setting a value specified by a ventilator, in particular a pressure, preferably a positive end-expiratory pressure (PEEP), is proposed, wherein the following steps are carried out: determining a local strain of a lung during artificial ventilation by means of a method for determining a local strain of a lung during artificial ventilation according to any one of claims 5 to 7; and adapting the value specified by the ventilator on the basis of the relative strain values ($STR_{RELATIV}$) formed.

The specific effects and advantages of this method have already been described above in respect of the system for automatically setting a value specified by a ventilator. In this respect, reference is made thereto.

In particular, the above-described value in the form of the relative strain value ($STR_{RELATIV}$) can be used to adapt the parameters for the artificial ventilation to the effect of a desired low value setting in (again) in the case of a strain that is too high, that is to say in the case of an elevated relative strain value ($STR_{RELATIV}$). Accordingly, the proposed method can reliably ensure that overexpansion, and also a collapse, of individual lung regions is avoided. By way of example, the PEEP can be reduced if a value that is too high, i.e., a value lying over a threshold, is measured as relative strain value. However, what is also essential here is that overexpansion or the strain can also be reliably detected during artificial ventilation when the PEEP is merely set to a low value.

The present invention also allows the overexpansion or the strain for the overall lung to be expressed in terms of a value. To this end, the totality of all pixel values of the lung area can be used as a basis. Thus, the mean overexpansion value or the mean strain of all pixels in the lung area can be determined by virtue of summing the strain values of all pixels and this sum being divided by the number of pixels in the lung area. Thus, different ventilation settings can be objectively compared to one another on the basis of a simple numerical value. Thus, the PEEP or else the tidal volume can be set in targeted fashion on the basis of this simple value.

The present invention can advantageously solve the problem of identifying lung strain in the case of a low PEEP. As soon as the lung collapses, the remaining residual lung tissue is reactively over-expanded. The greater the amount of the collapse, the more overexpansion occurs. Precisely this overexpansion can be made visible by the present invention. The user of the system can be encouraged to apply more PEEP as a reaction in order to increase the lung volume available for ventilation (EELI).

BRIEF DESCRIPTION OF THE DRAWINGS

The present invention is explained in more detail below with reference to the appended drawings, in which.

DETAILED DESCRIPTION OF EXEMPLARY EMBODIMENTS OF THE INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
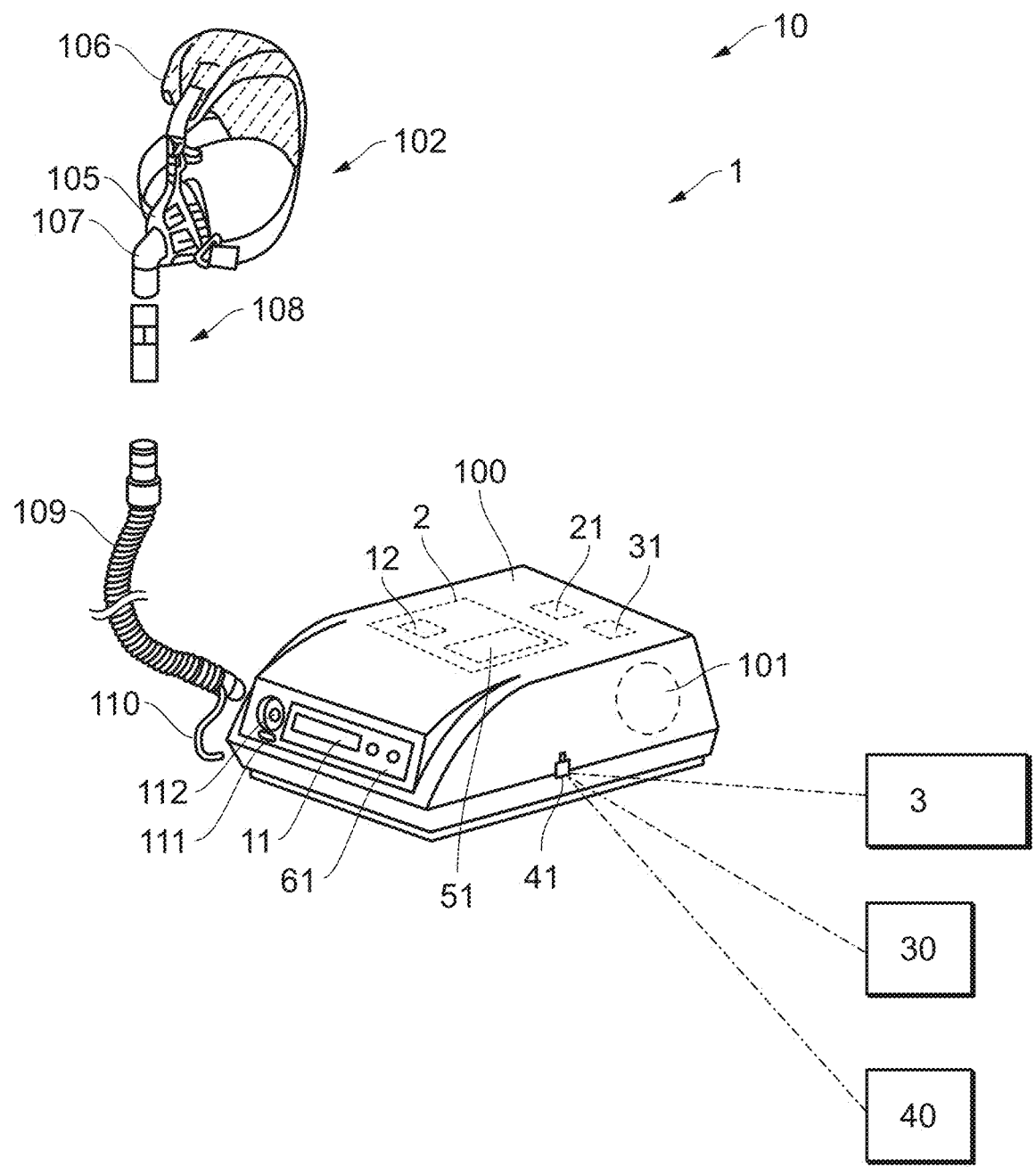
FIG. 1 shows a ventilator 1 according to the invention.

FIG. 1 shows a ventilator 1 according to the invention, which can be a home ventilator or sleep therapy device or a ventilator 1 used as a clinical ventilator. The ventilator 1 is embodied to carry out the method according to the invention. By way of example, the ventilator 1 is part of a system 10 that comprises an EIT apparatus.

The ventilator 1 comprises at least one controllable respiratory gas source 100 and a programmable control device 21

(closed-loop control device) and at least one sensor device 2 for determining pressure and/or flow of the respiratory gas, wherein the control device 21 drives the respiratory gas source to specify a first predetermined ventilation pattern (in respect of pressure, flow, volume, frequency). The ventilator moreover comprises at least two further sensor devices 3, 30, 40, which are spatially separated from the ventilator 1, for example, and which communicate with the control device 21 of the ventilator 1. A sensor 3 is embodied as an EIT (or EI) apparatus and comprises a multiplicity of individual sensor devices 3, 3', 3" . . . , and each sensor device is embodied to generate electrical potentials and/or to non-invasively determine the electrical impedance (EI) of a body section and to ascertain and transmit the sensor measured values to the control unit. The control device 21 evaluates the sensor measured values of the EI sensor device 3 for the purposes of determining the current ventilation or the strain of the lung during the ventilation with a first ventilation pattern. The control device 21 drives the respiratory gas source, for example also to specify a second ventilation pattern, which differs from the first ventilation pattern in terms of pressure and/or flow and/or volume and/or frequency, wherein the control device 21 evaluates the sensor measured values of the EI sensor device 3 for the purposes of determining the resultant ventilation or the strain of the lung during the ventilation with the second ventilation pattern, wherein the control device 21 compares the current ventilation or the strain with the resultant ventilation or the resultant strain, for the purposes of determining the better-suited ventilation pattern. By way of example, the control device adapts at least one pressure, for example the PEEP, or a ventilation pattern in such a way that the strain is reduced. By way of example, the strain is reduced by increasing the EPAP or the PEEP.

The ventilator 1 comprises a respiratory gas source 100 with, for example, a fan device and/or a valve device 101 for generating a respiratory gas flow for the ventilation. Here, a control device 21 is provided for controlling the respiratory gas source 100 and for capturing and processing sensor data. The ventilator 1 is operated and set by way of a user interface 61 comprising operating elements and a display device 11 (display).

The ventilator 1 comprises a respiratory interface 102 for supplying the respiratory gas flow to a patient for ventilation purposes. The respiratory interface 102 shown here is a respiration mask 105, embodied in exemplary fashion as a nasal mask or full mask, or a tube. By way of example, a headgear 106 is provided for securing the respiratory mask 105. By way of example, the respiratory interface 102 can also be configured as a full face mask, as a nasal mask, as a tube or as a laryngeal mask.

At least one connecting tube 109 is provided for connecting the respiratory interface 102 to the respiratory gas source 100, said connecting tube being connected in air-guiding fashion to the respiratory gas source 100 by way of a coupling device 112. The connecting tube 109 is connected to the respiratory interface 102 via a coupling element 107. An exhalation element 108, which comprises a valve or is embodied as such, is disposed between the connecting tube 109 and the coupling element 107. By way of example, the exhalation element 108 is provided to prevent respiration back into the ventilator 1 while the user exhales.

The control device 21 is connected to a sensor device 2, 3, 30, 40, not illustrated in any more detail, which comprises one or more sensors for capturing appliance parameters and/or patient parameters and/or other quantities characteristic for ventilation. The control device 21 can be embodied as a central control device which processes all sensor values, for example in the ventilator. The control device 21 can be configured in the form of a plurality of decentralized control devices, for example one in the ventilator and respectively one assigned to one sensor (or the sensors), having quantities characteristic for ventilation.

By way of example, the control device 21 comprises a pressure sensor 2, not shown in any more detail here, which ascertains the pressure conditions in the respiratory gas. To this end, the pressure sensor is operatively connected to the respiratory gas, for example via a pressure measuring tube 110 to the respiratory interface 102. The pressure measuring tube 110 is linked to the control device 21 via an input nozzle 111. By way of example, the control device 21 also comprises a flow sensor 2, not shown in any more detail here, which ascertains the flow conditions in the respiratory gas.

Moreover, the control device 21 is used here to drive the fan device and/or the valve device 101. The control device 21 provides a necessary minimum pressure and compensates pressure variations that are caused by the respiratory action of the user. By way of example, the control device 21 also captures the current pressure in the respiratory mask 105 and accordingly updates the power of the respiratory gas source until a desired ventilation pressure sets in.

The appliance parameters required to set the respiratory gas source 100 and the appliance configuration and/or appliance software are stored in a memory device 31.

The control device 21 can also regulate the oxygen content in the respiratory gas by appropriate driving of the fan device and/or the valve device 101, wherein the valve device has or contacts at least one oxygen source (pressurized gas mask or hospital line). By way of example, oxygen is admixed to the respiratory gas flow downstream or upstream of the fan device. In this case, the valve device is an oxygen mixing valve. Oxygen admixing into the respiratory gas flow is implemented, for example, by a valve unit that guides and regulates the respiratory gas flow and the oxygen flow.

The control device 21 can also be embodied to capture patient parameters captured by sensors. To this end, the control device 21 can be equipped with sensors for measuring the respiratory excursion, for measuring an oxygen supply and/or a carbon dioxide supply and/or for measuring an EEG, EMG, EOG or ECG activity.

In particular, the system 10 comprises at least two sensor devices 3, 30, 40 that are spatially separate from the ventilator 1 and that communicate with the control unit 21, wherein a sensor 3 has a multiplicity of individual sensor devices 3, 3', 3" . . . , and each sensor device is embodied to generate electrical potentials for non-invasively determining the electrical impedance EI of a body section. By way of example, the sensor devices 3 are embodied as adhesive plasters, with an outer layer distant from the skin and an adhesive layer facing the skin, or combined as a belt that holds the sensor devices.

By way of example, the ventilator also comprises at least one further sensor device 30, which is embodied to non-invasively determine a carbon dioxide ($CO_2$) value 30. By way of example, the sensor device 30 is embodied as a clamped sensor or as an adhesive plaster, with an outer layer distant from the skin and an adhesive layer facing the skin. The ventilator 10 comprises at least one further sensor device 40, which is embodied to non-invasively determine an oxygen ($O_2$) value 40. By way of example, the sensor device 40 is embodied as a clamped sensor or as an adhesive plaster, with an outer layer distant from the skin and an adhesive layer facing the skin. According to the invention, the CO2 value 30 and/or the O2 value 40 can be determined invasively or non-invasively in the tissue of the patient and/or non-invasively in the respiratory gas flow.

By way of example, the sensors 3, 30, 40 comprise power and transmission-means means for ascertaining and wirelessly transmitting the sensor measured values. Alternatively, the sensors 3, 30, 40 comprise, e.g., communication means for transmitting the sensor measured values to the controller 21.

Figure 2:
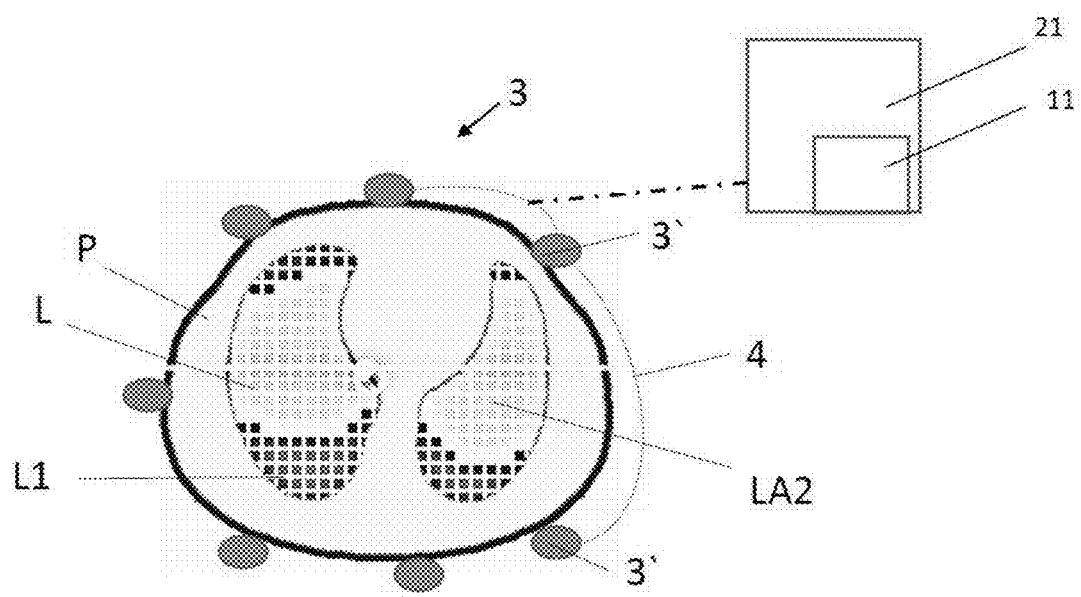
FIG. 2 shows a schematic illustration of an EIT measurement during ventilation.

FIG. 2 shows a schematic illustration of the EIT measurement during ventilation.

In exemplary fashion, the ventilator also comprises at least one further sensor device 3 for performing the EIT measurement.

By way of example, the sensor device has 32 high-resolution sensors 3, 3' . . . in a textile belt (not illustrated). An integrated relative position sensor (not illustrated) determines the position of the patient. The sensors are interconnected by communication or line means 4 and disposed in such a way that they can successively receive signals from all directions. Therefore, the control unit 21 can spatially assign the sensor measured values of the EIT measurement. Using this, it is possible to ascertain the local tissue resistances from different directions and then convert these into moving images. The control unit 21 processes the sensor measured values of the EIT measurement in such a way that a specific electrical impedance (EI) is ascertained for individual lung sections L1, LA2. The sensor device 3 is connected to the control unit 21 via wired or wireless communication means. The control unit 21 stores and processes the sensor measured values for use by the ventilator. The memory device 31 can be a constituent part of the control unit 21 or a separate component.

FIG. 2 also shows a schematic illustration of the results of the EIT measurement on the display of the ventilator. The control unit 21 processes the sensor measured values for use by the ventilator in such a way that, for example, a visualization of the patient thorax P with the two lungs L is presented on the display of the ventilator 10. The control unit 21 processes the sensor measured values of the EIT measurement 3 in such a way that a specific electrical impedance (EI) of the lung L is ascertained for individual lung sections L1, LA2. For the presentation on the display, the specific electrical impedance (EI) of the lung sections L1, LA2 is prepared in such a way that lung sections with a high electrical impedance LA2 are represented differently from a graphical point of view than the lung sections with a low electrical impedance L1. The control unit 21 processes the sensor measured values of the EIT measurement 3 in respect of time in such a way that a specific electrical impedance EI of the lung L is ascertained per breath for individual lung sections L1, LA2 and prepared for presentation on the display.

The sensor device 3 is also configured and embodied (together with the controller and the memory) to form an EIT summed signal, for example, which is a measure for the ventilation of the lung or of lung sections. The sensor device 3 is also configured and embodied (together with the controller and the memory) to ascertain a frequency of the EIT change frequency. Consequently, in summary, the sensor device 3 can ascertain the current ventilation.

Within the meaning of the invention, the EIT summed signal is understood to mean that the impedance distribution or impedance change distribution in the sectional plane determined by the sensors or in the volume spanned by the sensors need not necessarily be presented pictorially, for example on a display, for the purposes of performing the method according to the invention but at least that the calculated result values of the impedance distribution or impedance change distribution are available for performing the method in the apparatus according to the invention.

Accordingly, when summing all impedance values of the sensors, there is a modified summed signal during inspiration in comparison with the summed signal during expiration. Accordingly, the summed value represents an adequate measure for determining the ventilation of the lung.

The EIT change frequency can be determined from the respiratory phase-dependent change in the impedance values of the sensors. The impedance values of the sensors vary in respiratory phase-dependent fashion with inspiration and expiration. Accordingly, the EIT change frequency represents an alternative or complementary measure for determining the (frequency of the) ventilation of the lung.

By way of example, the sensors are integrated, together with a relative position sensor, in a textile and breathable and stretchable electrode belt. The sensor 3 and the control unit are configured to generate a frame rate of, e.g., up to 50 frames per second. Lung regions LA are visualized in the process. According to the invention, patient-related inputs are possible, such as height, weight, sex, chest size.

The EIT data ascertained and prepared thus facilitate a temporally and spatially resolved differential analysis and representation of the electrical impedance EI of the lung.

Figure 3:
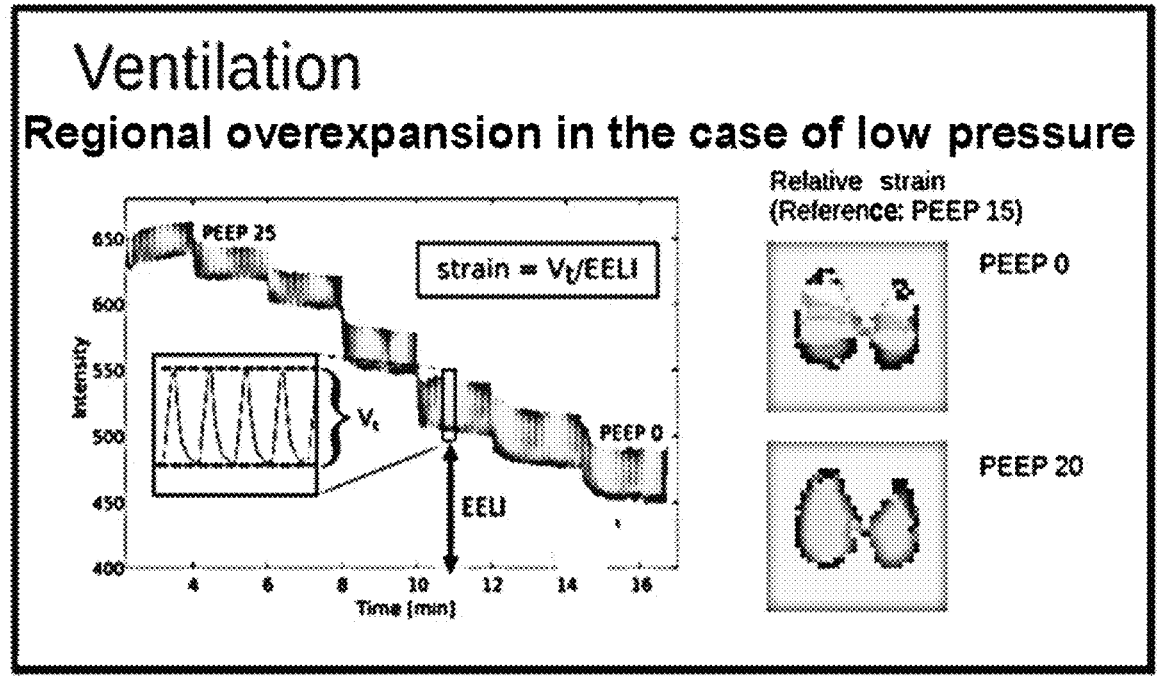
FIG. 3 schematically shows an ascertainment of the local lung overexpansion on the basis of measurement of deformations caused by respiration in the case of a low PEEP.

FIG. 3 shows the ascertainment of the local lung overexpansion on the basis of measurement of deformations caused by respiration in the case of a low PEEP.

All calculations were performed within the individual lung region of interest (ROI), which was formed by the pixels whose amplitude was greater than x % of the amplitude of the pixel with the maximum respiratory-caused impedance change in the case of PEEP 30.

According to the invention, the strain of the whole lungs, which causes the deformation of the lung tissue caused by breathing, can be estimated as follows:

$$\text{strain} = VT/FRC$$

The calculation of the local strain using this novel EIT-based approach is implemented at a pixel level, by virtue of the tidal volume of each pixel being determined from its respective change in impedance (delta Z) during the respiratory cycle and said tidal volume thereupon being related to its respective end-expiratory volume, which corresponds to its impedance value at the end of expiration (EELI). The corresponding formula therefore reads:

$$\text{Strain} = Z_{\text{end-expiration}} - Z_{\text{end-inspiration}} / EELI = \text{Delta } Z/EELI$$

Zend-expiration, Zend-inspiration and EELI were ascertained for each pixel and each breath, the respective mean value was calculated therefrom over all measured breaths at a respective PEEP level and the strain of each pixel was then calculated therefrom.

Subsequently, the pixel strain at each PEEP level was related to the individual pixel strain in the case of the reference PEEP of 15 cm H2O, as result of which a normalization was obtained, the latter facilitating the creation of comparable relative strain images, which formed the basis for the calculation of numerical values of the total strain for the respective PEEP level. To this end, the respective pixel values were summed and normalized with respect to the number of all pixels in the lung ROI of each pig. Finally, EIT images were generated from the aforementioned strain images, said EIT images representing the mean relative strain of all subjects at the respective PEEP level.

According to the invention, the measurement and closed-loop control technology of the ventilator is linked to electrical impedance tomography (EIT). This allows the function of the lung to be continuously presented in imaging fashion. The measured values of the ventilator are combined with the results of the electrical impedance tomography examination. Thus, this technology allows very different clinical questions to be assessed and the therapy to be adjusted accordingly.

To sum up, the present invention provides:

1. A system for real-time determination of a local strain of a lung during artificial ventilation using a ventilator, wherein the system comprises a device for electrical impedance tomography (EIT), which device is configured to capture an electrical impedance distribution along at least one two-dimensional section through a human thorax, and further comprises a device for assigning the captured electrical impedance distribution, for dividing the captured electrical impedance distribution at different times during the artificial ventilation into a multiplicity of EIT pixels, and for assigning a specific value of the electrical impedance at a specific time to a specific EIT pixel.
2. The system of item 1, which further comprises a device for determining a local strain value, which device is configured to determine at least one end-inspiratory electrical impedance ($Z_{INSP}$) of the specific EIT pixel and one end-expiratory electrical impedance ($Z_{EXSP}$) of the specific EIT pixel.
3. The system of item 2, wherein the device is configured to form a local tidal volume reference value ($\Delta Z$) of the specific EIT pixel as a difference between an end-inspiratory electrical impedance ($Z_{INSP}$) and an end-expiratory electrical impedance ($Z_{EXSP}$).
4. The system of item 2, wherein the device is configured to form a local tidal volume reference value ($\Delta Z$) of the specific EIT pixel as a difference between an end-inspiratory electrical impedance ($Z_{INSP}$) and an end-expiratory electrical impedance ($Z_{EXSP}$) by subtracting the end-expiratory electrical impedance ($Z_{EXSP}$) from the end-inspiratory electrical impedance ($Z_{INSP}$).
5. The system of any one of the preceding items, wherein the device is configured to form a preliminary strain value ($STR_{VORL}$) of the specific EIT pixel by dividing a local tidal volume reference value ($\Delta Z$) by an end-expiratory electrical impedance ($Z_{EXSP}$).
6. The system of any one of the preceding items, wherein the device is configured to form a relative strain value ($STR_{RELATIV}$) of a specific EIT pixel by normalizing a preliminary strain value ($STR_{VORL}$) to a reference strain value ($STR_{REF}$).
7. The system of any one of the preceding items, wherein the device is configured to normalize a preliminary strain value ($STR_{VORL}$) to a quotient of a local tidal volume reference value ($\Delta Z$) and an end-expiratory electrical impedance ($Z_{EXSP}$) of a specific EIT pixel at a specified positive end-expiratory pressure (PEEP).
8. The system of any one of the preceding items, wherein the system comprises a device for electrical impedance tomography (EIT), which device is configured to capture an electrical impedance distribution along at least one two-dimensional section through a human thorax, and further comprises a device for assigning the captured electrical impedance distribution, for dividing the captured electrical impedance distribution at different times during the artificial ventilation into a multiplicity of EIT pixels and for assigning a specific value of the electrical impedance at a specific time to a specific EIT pixel;
wherein the system further comprises a device for determining a local strain value, which device is configured to determine at least one end-inspiratory electrical impedance ($Z_{INSP}$) of the specific EIT pixel and an end-expiratory electrical impedance ($Z_{EXSP}$) of the specific EIT pixel,
to form a local tidal volume reference value ($\Delta Z$) of the specific EIT pixel as a difference between the end-inspiratory electrical impedance ($Z_{INSP}$) and the end-expiratory electrical impedance ($Z_{EXSP}$), in particular by subtracting the end-expiratory electrical impedance ($Z_{EXSP}$) from the end-inspiratory electrical impedance ($Z_{INSP}$), and
to form a preliminary strain value ($STR_{VORL}$) of the specific EIT pixel by dividing the local tidal volume reference value ($\Delta Z$) by the end-expiratory electrical impedance ($Z_{EXSP}$);
and wherein the device for determining a local strain value is further configured to form a relative strain value ($STR_{RELATIV}$) of the specific EIT pixel by normalizing the preliminary strain value ($STR_{VORL}$) to a reference strain value ($STR_{REF}$).
9. The system of any one of the preceding items, wherein the device for electrical impedance tomography (EIT) is coupled to the ventilator or is part of the ventilator.
10. A system for automatically setting a value specified by a ventilator, in particular a pressure, preferably a positive end-expiratory pressure (PEEP), wherein the system comprises the system of any one of the preceding claims and a closed-loop control device that is configured to adapt a value specified by the ventilator on the basis of relative strain values ($STR_{RELATIV}$) formed.
11. A method for determining a local strain of a lung during artificial ventilation, in particular to be performed in the system of any one of the preceding items, wherein the method comprises:

capturing an electrical impedance distribution along at least one two-dimensional section through a human thorax by a device for electrical impedance tomography (EIT), dividing the captured electrical impedance distribution at different times during the artificial ventilation into a multiplicity of EIT pixels, assigning a specific value of the electrical impedance to a specific EIT pixel at a specific time, determining at least one end-inspiratory electrical impedance ($Z_{INSP}$) of the specific EIT pixel and an end-expiratory electrical impedance ($Z_{EXSP}$) of the specific EIT pixel, forming a local tidal volume reference value ($\Delta Z$) of the specific EIT pixel as a difference between the end-inspiratory electrical impedance ($Z_{INSP}$) and the end-expiratory electrical impedance ($Z_{EXSP}$), in particular by subtracting the end-expiratory electrical impedance ($Z_{EXSP}$) from the end-inspiratory electrical impedance ($Z_{INSP}$), forming a preliminary strain value ($STR_{VORL}$) of the specific EIT pixel by dividing the local tidal volume reference value ($\Delta Z$) by the end-expiratory electrical impedance ($Z_{EXSP}$), and forming a relative strain value ($STR_{RELATIV}$) of the specific EIT pixel by normalizing the preliminary strain value ($STR_{VORL}$) to a reference strain value ($STR_{REF}$).

12. The method of item 11, wherein the reference strain value ($STR_{REF}$) is formed as a quotient of the local tidal volume reference value ($\Delta Z$) and the end-expiratory electrical impedance ($Z_{EXSP}$) of the specific EIT pixel at a specified positive end-expiratory pressure (PEEP).

13. The method of item 11 or item 12, wherein a relevant lung area is initially identified.

14. A method for automatically setting a value specified by a ventilator, in particular a pressure, preferably a positive end-expiratory pressure (PEEP), wherein the method comprises:
determining a local strain of a lung during artificial ventilation by the method of any one of items 11 to 13; and
adapting the value specified by the ventilator based on the relative strain values ($STR_{RELATIV}$) formed.

15. A ventilator, configured and embodied for use in the system of any one of items 1 to 11 and/or for carrying out the method of any one of items 11 to 14.

16. A ventilator, in particular according to item 15, wherein the ventilator is configured and embodied to perform the global strain of the lungs, which causes the respiration-dependent deformation of the lung tissue, using the EIT information at a pixel level.

17. A ventilator, in particular according to item 15, wherein the ventilator is configured and embodied to perform a determination of the local strain of the lung using the EIT information at a pixel level, by virtue of the tidal volume of each pixel being determined from its respective change in impedance (delta Z) during the respiratory cycle and said tidal volume thereupon being related to its respective end-expiratory volume, which corresponds to its impedance value at the end of expiration (EELI).

18. A ventilator, in particular according to item 15, wherein the ventilator comprises at least one controllable respiratory gas source, a (programmable) control device (closed-loop control device), and at least one sensor device for determining pressure and/or flow of a respiratory gas, wherein the control device drives the respiratory gas source for specifying a first predetermined ventilation pattern (in respect of pressure, flow, volume, frequency), wherein the ventilator further comprises at least one sensor device that is spatially separated from the ventilator and communicates with the control device of the ventilator, wherein the sensor device is configured to generate electrical potentials and/or to non-invasively determine the electrical impedance (EI) of a body section and to determine and transfer the sensor measured values to the control unit, wherein the control device evaluates the sensor measured values of the EI sensor device for the purposes of determining the current strain of the lung during the ventilation with a first ventilation pattern and wherein the control device drives the respiratory gas source for specifying a second ventilation pattern, which differs from the first ventilation pattern in terms of pressure and/or flow and/or volume and/or frequency, and wherein the control device evaluates the sensor measured values of the EI sensor device for the purposes of determining a resultant strain or strain of the lung during the ventilation with the second ventilation pattern.

19. The ventilator of item 18, wherein the control device adapts at least one pressure, for example the PEEP, or a ventilation pattern in such a way that the strain is reduced.

20. The ventilator of item 18 or item 19, wherein the control device increases the PEEP in order to reduce the strain.

21. The ventilator of any one of items 18 to 20, wherein the control device specifies the pressure during expiration based on the strain.

22. The ventilator of any one of claims 15 to 21, wherein the ventilator is configured and embodied to determine a local strain of a lung during artificial ventilation and wherein the following steps are carried out:
capturing an electrical impedance distribution along at least one two-dimensional section through a human thorax by means of a device for electrical impedance tomography (EIT),
dividing the captured electrical impedance distribution at different times during the artificial ventilation into a multiplicity of EIT pixels,
assigning a specific value of the electrical impedance to a specific EIT pixel at a specific time,
determining at least one end-inspiratory electrical impedance ($Z_{INSP}$) of the specific EIT pixel and an end-expiratory electrical impedance ($Z_{EXSP}$) of the specific EIT pixel,
forming a local tidal volume reference value ($\Delta Z$) of the specific EIT pixel as a difference between the end-inspiratory electrical impedance ($Z_{INSP}$) and the end-expiratory electrical impedance ($Z_{EXSP}$), in particular by subtracting the end-expiratory electrical impedance ($Z_{EXSP}$) from the end-inspiratory electrical impedance ($Z_{INSP}$),
forming a preliminary strain value ($STR_{VORL}$) of the specific EIT pixel by dividing the local tidal volume reference value ($\Delta Z$) by the end-expiratory electrical impedance ($Z_{EXSP}$), and
forming a relative strain value ($STR_{RELATIV}$) of the specific EIT pixel by normalizing the preliminary strain value ($STR_{VORL}$) to a reference strain value ($STR_{REF}$).

What is claimed is:

1. A system for real-time determination of a local strain of a lung during artificial ventilation using a ventilator, wherein the system comprises a device for electrical impedance tomography (EIT), which device is configured to capture an electrical impedance distribution along at least one two-dimensional section through a human thorax, and further comprises a device for assigning the captured electrical impedance distribution, dividing the captured electrical impedance distribution at different times during the artificial ventilation into a multiplicity of EIT pixels and assigning a specific value of the electrical impedance at a specific time to a specific EIT pixel;
wherein the system further comprises a device for determining a local strain value which device is configured to determine at least one end-inspiratory electrical impedance ($Z_{INSP}$) of the specific EIT pixel and an end-expiratory electrical impedance ($Z_{EXSP}$) of the specific EIT pixel, to form a local tidal volume reference value ($\Delta Z$) of the specific EIT pixel as a difference between the end-inspiratory electrical impedance ($Z_{INSP}$) and the end-expiratory electrical impedance ($Z_{EXSP}$), in particular by subtracting the end-expiratory electrical impedance ($Z_{EXSP}$) from the end-inspiratory electrical impedance ($Z_{INSP}$), and
to form a preliminary strain value ($STR_{VORL}$) of the specific EIT pixel by dividing the local tidal volume reference value ($\Delta Z$) by the end-expiratory electrical impedance ($Z_{EXSP}$);

and wherein the device for determining a local strain value is further configured to form a relative strain value ($STR_{RELATIV}$) of the specific EIT pixel by normalizing the preliminary strain value ($STR_{VORL}$) to a reference strain value ($STR_{REF}$).

2. The system of claim 1, wherein the device for determining a local strain value is configured to normalize the preliminary strain value ($STR_{VORL}$) to a quotient of the local tidal volume reference value ($\Delta Z$) and an end-expiratory electrical impedance ($Z_{EXSP}$) of a specific EIT pixel at a specified positive end-expiratory pressure (PEEP).

3. The system of claim 1, wherein the device for electrical impedance tomography (EIT) is coupled to the ventilator or is part of the ventilator.

4. A system for automatically setting a value specified by a ventilator, wherein the system comprises the system of claim 1 and a closed-loop control device that is configured to adapt the value specified by the ventilator on the basis of relative strain values ($STR_{RELATIV}$) formed.

5. The system of claim 1, wherein the system further comprises the ventilator.

6. The system of claim 5, wherein the ventilator is configured and embodied to perform the local strain of the lungs, which causes a respiration-dependent deformation of the lung tissue, using EIT information at a pixel level.

7. The system of claim 5, wherein the ventilator is configured and embodied to perform a determination of the local strain of the lung using EIT information at a pixel level, by virtue of a tidal volume of each pixel being determined from its respective change in impedance (delta Z) during a respiratory cycle and said tidal volume thereupon being related to its respective end-expiratory volume, which corresponds to its impedance value at the end of expiration (EELI).

8. The system of claim 5, wherein the ventilator comprises at least one controllable respiratory gas source, a control device, and at least one sensor device for determining pressure and/or flow of a respiratory gas, wherein the control device drives the respiratory gas source for specifying a first predetermined ventilation pattern (in respect of pressure, flow, volume, frequency), wherein the control device is configured to communicate with the device for electrical impedance tomography that is spatially separated from the ventilator device, wherein the control device evaluates sensor measured values of the device for electrical impedance tomography for determining a current strain of the lung during ventilation with the first ventilation pattern and wherein the control device drives the at least one respiratory gas source for specifying a second ventilation pattern, which differs from the first ventilation pattern in terms of pressure and/or flow and/or volume and/or frequency, wherein the control device evaluates sensor measured values of the device for electrical impedance tomography determining a resultant strain of the lung during the ventilation with the second ventilation pattern.

9. The system of claim 8, wherein the control device adapts at least one pressure or a ventilation pattern in such a way that the strain is reduced and/or increases PEEP in order to reduce the strain and/or specifies the pressure during expiration based on the strain.

10. A method for determining a local strain of a lung during artificial ventilation, wherein the method comprises:
capturing an electrical impedance distribution along at least one two-dimensional section through a human thorax by a device for electrical impedance tomography (EIT),
dividing the captured electrical impedance distribution at different times during the artificial ventilation into a multiplicity of EIT pixels,
assigning a specific value of the electrical impedance to a specific EIT pixel at a specific time,
determining at least one end-inspiratory electrical impedance ($Z_{INSP}$) of the specific EIT pixel and an end-expiratory electrical impedance ($Z_{EXSP}$) of the specific EIT pixel,
forming a local tidal volume reference value ($\Delta Z$) of the specific EIT pixel as a difference between the end-inspiratory electrical impedance ($Z_{INSP}$) and the end-expiratory electrical impedance ($Z_{EXSP}$), in particular by subtracting the end-expiratory electrical impedance ($Z_{EXSP}$) from the end-inspiratory electrical impedance ($Z_{INSP}$),
forming a preliminary strain value ($STR_{VORL}$) of the specific EIT pixel by dividing the local tidal volume reference value ($\Delta Z$) by the end-expiratory electrical impedance ($Z_{EXSP}$), and
forming a relative strain value ($STR_{RELATIV}$) of the specific EIT pixel by normalizing the preliminary strain value ($STR_{VORL}$) to a reference strain value ($STR_{REF}$).

11. The method of claim 10, wherein the reference strain value ($STR_{REF}$) is formed as a quotient of the local tidal volume reference value ($\Delta Z$) and the end-expiratory electrical impedance ($Z_{EXSP}$) of the specific EIT pixel at a specified positive end-expiratory pressure (PEEP).

12. A method for automatically setting a value specified by a ventilator, wherein the method comprises:
determining a local strain of a lung during artificial ventilation by the method of claim 10; and
adapting the value specified by the ventilator on the basis of the relative strain values ($STR_{RELATIV}$) formed.

13. A ventilator, configured and embodied for carrying out the method of claim 10.

* * * * *